(12) United States Patent
Arch et al.

(10) Patent No.: US 7,241,756 B2
(45) Date of Patent: *Jul. 10, 2007

(54) COMBINATIONS OF DIPEPTIDYL PEPTIDASE IV INHIBITORS AND OTHER ANTIDIABETIC AGENTS FOR THE TREATMENT OF DIABETES MELLITUS

(75) Inventors: Jonathan Robert Sanders Arch, Harlow (GB); James Martin Lenhard, Durham County, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/421,548

(22) Filed: Jun. 1, 2006

(65) Prior Publication Data

US 2006/0205675 A1    Sep. 14, 2006

Related U.S. Application Data

(63) Continuation of application No. 10/311,446, filed on Feb. 20, 2003, now Pat. No. 7,078,397.

(30) Foreign Application Priority Data

Jun. 19, 2000   (GB) ................... 0014969.0

(51) Int. Cl.
     *A61K 31/43*      (2006.01)
(52) U.S. Cl. .............. 514/193; 514/275; 514/255.06; 514/3; 514/342; 514/343; 514/369; 514/423; 514/470; 514/492; 514/563; 514/592
(58) Field of Classification Search ............. 514/193
     See application file for complete search history.

(56) References Cited

U.S. PATENT DOCUMENTS 6,274,608 B1 *   8/2001   Sauerberg et al. .......... 514/369

2001/0016586 A1 *   8/2001   Guitard et al. ......... 514/255.06
2003/0139434 A1 *   7/2003   Balkan et al. .............. 514/275

FOREIGN PATENT DOCUMENTS

| EP | 0 306 228 | 3/1989 |
| WO | WO-98/19998 | 5/1998 |
| WO | WO-99/61431 | 12/1999 |
| WO | WO-01/52825 | 7/2001 |

OTHER PUBLICATIONS

Deacon et al.; "Dipeptidyl Peptidase IV Inhibition Potentiates the Insulinotropic Effect of Glucogen-like Peptide 1 in the Anethesized Pig"; Diabetes; 1998; 47/5; pp. 764-769.
Hoffamn et al.; Diabetes Care; 1992; 15/8; pp. 1075-1078.
Holst et al; "Inhibition of the Activity of Dipeptidyl-Peptidase IV as a Treatment for Type 2 Diabetes"; Diabetes; 1998; 47; pp. 1663-1670.
Hotta; Chronic Disease; 1995; 6/1; pp. 97-102.
Hotta; Tonyobo Update; 1994; 10; pp. 68-77.
Lebovitz; Diabetes Care; 1994; 17/12; pp. 1542-1544.
Pauly et al.; "Improved Glucose Tolerance in Rats Treated with the Dipeptidyl Peptidase IV (CD26) Inhibitor Ile-Thiazolidide"; Metabolism, Clinical and Experimental; 1999; 48/3; pp. 385-389.
Williams; Lancet; 1994; 343; pp. 95-100.

* cited by examiner

*Primary Examiner*—Cecilia J. Tsang
*Assistant Examiner*—Maury Audet
(74) *Attorney, Agent, or Firm*—Amy H. Fix

(57) ABSTRACT

A method for the treatment of diabetes mellitus, especially Type 2 diabetes and conditions associated with diabetes mellitus in a mammal such as a human, which method comprises administering an effective, non-toxic and pharmaceutically acceptable amount of a dipeptidyl peptidase IV inhibitor and another antidiabetic agent, to a mammal in need thereof.

3 Claims, No Drawings

COMBINATIONS OF DIPEPTIDYL PEPTIDASE IV INHIBITORS AND OTHER ANTIDIABETIC AGENTS FOR THE TREATMENT OF DIABETES MELLITUS

This application is a continuation of U.S. Ser. No. 10/311,446, files on Feb. 20, 2003, now U.S. Pat. No. 7,078,397.

This invention relates to a method of treatment, in particular to a method for the treatment of diabetes mellitus, especially non-insulin dependent diabetes (NIDDM) or Type 2 diabetes and conditions associated with diabetes mellitus and to compositions for use in such method.

Dipeptidyl peptidase IV (DPP-IV) is a post-proline/alanine cleaving serine protease found in various tissues of the body including kidney, liver, and intestine.

It is known that DPP-IV inhibitorsare may be useful for the treatment of impaired glucose tolerance and diabetes mellitus (International Patent Application, Publication Number WO99/61431, Pederson R A et al, Diabetes. 1998 Aug;47(8):1253-8 and Pauly R P et al, Metabolism 1999 Mar;48(3):385-9). In particular WO99/61431 discloses DPP-IV inhibit comprising an amino acid and a thiazolidine or pyrrolidine group, and salts therefore, such as isoleucvl (or isoleucine) thiazolidide and salts thereof.

Other DPP-IV inhibitors include those disclosed in U.S. Pat. No. 6,124,305 and U.S. Pat. No. 6,107,317, International Patent Applications, Publication Numbers WO 9819998, WO 9515309 and WO 9818763.

Alpha glucosidase inhibitor antihyperglycaemic agents (or alpha glucosidase inhibitors) and biguanide antihyperglycaemic agents (or biguanides) are commonly used in the treatment of Type 2 diabetes. Acarbose, voglibose, emiglitate and miglitol are examples of alpha glucosidase inhibitors. 1,1-Dimethylbiguanidine (or metformin) is a particular example of a biguanide.

Insulin secretagogues are compounds that promote increased secretion of insulin by the pancreatic beta cells. The sulphonylureas are well known examples of insulin secretagogues. The sulphonylureas act as hypoglycaemic agents and are used in the treatment of Type 2 diabetes. Examples of sulphonylureas include glibenclamide (or glyburide), glipizide, gliclazide, glimepiride, tolazamide and tolbutamide.

European Patent Application, Publication Number 0,306,228 relates to certain thiazolidinedione derivatives disclosed as having antihyperglycaemic and hypolipidaemic activity. One particular thiazolidinedione disclosed in EP 0306228 is 5-[4-[2-(N-methyl-N-(2-pyridyl)amino)ethoxy]benzyl]thiazolidine-2,4-dione (hereinafter 'Compound (I)'). WO94/05659 discloses certain salts of Compound (I) including the maleate salt at example 1 thereof.

Compound (I) is an example of a class of anti-hyperglycaemic agents known as 'insulin sensitisers'. In particular Compound (I) is a thiazolidinedione insulin sensitiser. Compound (I) is also a peroxisome proliferator-activated receptor (PPARγ) agonist insulin sensitiser.

European Patent Applications, Publication Numbers: 0008203, 0139421, 0032128, 0428312, 0489663, 0155845, 0257781, 0208420, 0177353, 0319189, 0332331, 0332332, 0528734, 0508740; International Patent Application, Publication Numbers 92/18501, 93/02079, 93/22445 and U.S. Pat. Nos. 5,104,888 and 5,478,852, also disclose certain thiazolidinedione insulin sensitisers.

Another series of compounds generally recognised as having insulin sensitiser activity are those typified by the compounds disclosed in International Patent Applications, Publication Numbers WO93/21166 and WO94/01420. These compounds are herein referred to as 'acyclic insulin sensitisers'. Other examples of acyclic insulin sensitisers are those disclosed in U.S. Pat. No. 5,232,945 and International Patent Applications, Publication Numbers WO92/03425 and WO91/19702.

Examples of other insulin sensitisers are those disclosed in European Patent Application, Publication Number 0533933, Japanese Patent Application Publication Number 05271204 and U.S. Pat. No. 5,264,451.

The above mentioned publications are incorporated herein by reference.

It is now indicated that dipeptidyl peptidase IV inhibitors, such as the compounds of WO99/61431, in combination with other antidiabetic agents provide a particularly beneficial effect on glycaemic control and that such combination is therefore suggested to be particularly useful for the treatment of diabetes mellitus, especially Type 2 diabetes and conditions associated with diabetes mellitus. Such combinations will provide improved blood glucose regulation without introducing unacceptable side-effects.

Accordingly, the invention provides a method for the treatment of diabetes mellitus, especially Type 2 diabetes and conditions associated with diabetes mellitus in a mammal such as a human, which method comprises administering an effective, non-toxic and pharmaceutically acceptable amount of a dipeptidyl peptidase IV inhibitor and another antidiabetic agent, to a mammal in need thereof.

In another aspect the invention provides a dipeptidyl peptidase IV inhibitor and another antidiabetic agent, for use in a method for the treatment of diabetes mellitus, especially Type 2 diabetes and conditions associated with diabetes mellitus.

The method comprises either co-administration of a dipeptidyl peptidase IV inhibitor and another antidiabetic agent or the sequential administration thereof.

Co-administration includes administration of a formulation which includes both a DPP-IV inhibitor and the other antidiabetic agent or the essentially simultaneous administration of separate formulations of each agent.

In another aspect the invention provides the use of a dipeptidyl peptidase IV inhibitor and another antidiabetic agent for use in the manufacture of a composition for the treatment of obesity, diabetes mellitus, especially Type 2 diabetes and conditions associated with diabetes mellitus.

Suitably, the other antidiabetic agent comprises one or more, generally one or two, of an alpha glucosidase inhibitor, a biguanide, an insulin secretagogue or an insulin sensitiser.

Suitably, the other antidiabetic agent is selected from an alpha glucosidase inhibitor, a biguanide, an insulin secretagogue or an insulin sensitiser.

A further suitable antidiabetic agent is insulin.

A suitable alpha glucosidase inhibitor is acarbose.

Other suitable alpha glucosidase inhibitors are emiglitate and miglitol. A further suitable alpha glucosidase inhibitor is voglibose.

Suitable biguanides include metformin, buformin or phenformin, especially metformin.

Suitable insulin secretagogues include sulphonylureas.

Suitable sulphonylureas include glibenclamide, glipizide, gliclazide, glimepiride, tolazamide and tolbutamide. Further sulphonylureas include acetohexamide, carbutamide, chlorpropamide, glibomuride, gliquidone, glisentide, glisolamide, glisoxepide, glyclopyamide and glycylamide. Also included is the sulphonylurea glipentide.

A further suitable insulin secretagogue is repaglinide. An additional insulin secretagogue is nateglinide.

Insulin sensitisers include PPARγ agonist insulin sensitisers including the compounds disclosed in WO 97/31907 and especially 2-(1-carboxy-2-{4-{2-(5-methyl-2-phenyl-oxazol-4-yl)-ethoxy]-phenyl}-ethylamino)-benzoic acid methyl ester and 2(S)-(2-benzoyl-phenylamino)-3-{4-[2-(5-methyl-2-phenyl-oxazol-4-yl)-ethoxyl]-phenyl}-propionic acid.

Insulin sensitisers also include thiazolidinedione insulin sensitisers.

A preferred insulin sensitiser is Compound (I) or a derivative thereof.

Other suitable thiazolidinedione insulin sensitisers include (+) -5-[[4-[(3,4-dihydro-6-hydroxy-2,5,7,8-tetramethyl-2H-1-benzopyran-2-yl)methoxy]phenyl]methyl]-2,4-thiazolidinedione (or troglitazone), 5-[4-[(1-methylcyclohexyl)methoxy]benzyl]thiazolidine-2,4-dione (or ciglitazone), 5-[4-[2-(5-ethylpyridin-2-yl)ethoxy]benzyl] thiazolidine-2,4-dione (or pioglitazone) or 5-[(2-benzyl-2,3-dihydrobenzopyran)-5-ylmethyl)thiazolidin-2,4-dione (or englitazone).

A particular thiazolidinedione insulin sensitiser is 5-[4-[2-(5-ethylpyridin-2-yl)ethoxy]benzyl] thiazolidine-2,4-dione (or piogilitazone).

A particular thiazolidinedione insulin sensitiser is (+)-5-[[4-[(3,4-dihydro-6-hydroxy-2,5,7,8-tetramethyl-2H-1-benzopyran-2-yl)methoxy]phenyl]methyl]-2,4-thiazolidinedione (or troglitazone).

Particular DPP-IV inhibitors include the specific examples disclosed in WO99/61431, such as L-threo-isoleucyl pyrrolidide, L-allo-isoleucyl thiazolidide, L-allo-isoleucyl pyrrolidide and salts thereof. A particular DPP-IV inhibitor is isoleucine thiazolidide and salts thereof.

Further DPP-IV inhibitors include the specific examples disclosed in U.S. Pat. Nos. 6,124,305 and U.S. Pat. No. 6,107,317, International Patent Applications, Publication Numbers WO 9819998, WO 9515309 and WO 9818763; such as 1[2-[(5-cyanopyridin-2-yl)aminoethylamino]acetyl-2-cyano-(S)-pyrrolidine and (2S)-1-[(2S)-2-amino-3,3-dimethylbutanoyl]-2-pyrrolidinecarbonitrile.

For the avoidance of doubt, the examples disclosed in each of the above mentioned publications are specifically incorporated herein by reference, as individually disclosed compounds.

It will be understood that the DPP-IV inhibitor and the other antidabetic agent are each administered in a pharmaceutically acceptable form, including pharmaceutically acceptable derivatives such as pharmaceutically acceptable salts, esters and solvates thereof, as appropriate of the relevant pharmaceutically active agent. In certain instances herein the names used for the other antidiabetic agent may relate to a particular pharmaceutical form of the relevant active agent. It will be understood that all pharmaceutically acceptable forms of the active agents per se are encompassed by this invention.

Suitable pharmaceutically acceptable forms of the other antidiabetic agent depend upon the particular agent being used but include known pharmaceutically acceptable forms of the particular agent chosen. Such derivatives are found or are referred to in standard reference texts such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

Suitable pharmaceutically acceptable forms of the DPP-IV inhibitor include salted forms and solvated forms, include those described in WO 99/61431, for example the fumarate salt The DPP-IV inhibitor is prepared according to published methods, for example when the DPP-IV inhibitor is a compound of WO 99/61431 or a derivative thereof such as a pharmaceutically acceptable salt thereof or a pharmaceutically acceptable solvate thereof, then it is prepared according to methods disclosed therein. Similarly for the compounds of U.S. Pat. No. 6,124,305 and U.S. Pat. No. 6,107,317 and those of International Patent Applications, Publication Numbers WO 9819998, WO 9515309 and WO 9818763.

Certain of the compounds mentioned herein may contain one or more chiral carbon atoms and hence can exist in two or more isomeric forms, all of which are encompassed by the invention, either as individual isomers or as mixtures of isomers, including racemates. Certain of the compounds mentioned herein, in particular the thiazolidinediones such as Compound (I), may exist in one of several tautomeric forms, all of which are encompassed by the invention as individual tautomeric forms or as mixtures thereof The DPP-IV inhibitor and the other antidiabetic agent of choice is prepared according to known methods, such methods are found or are referred to in standard reference texts, such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

When used herein the term 'conditions associated with diabetes' includes those conditions associated with the pre-diabetic state, conditions associated with diabetes mellitus itself and complications associated with diabetes mellitus.

When used herein the term 'conditions associated with the pre-diabetic state' includes conditions such as insulin resistance, including hereditary insulin resistance, impaired glucose tolerance and hyperinsulinaemia.

'Conditions associated with diabetes mellitus itself' include hyperglycaemia, insulin resistance, including acquired insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance and gestational diabetes.

'Complications associated with diabetes mellitus' includes renal disease, especially renal disease associated with Type 2 diabetes, neuropathy and retinopathy.

Renal diseases associated with Type 2 diabetes include nephropathy, glomerulonephritis, glomerular sclerosis, nephrotic syndrome, hypertensive nephrosclerosis and end stage renal disease.

As used herein the term 'pharmaceutically acceptable' embraces both human and veterinary use: for example the term 'pharmaceutically acceptable' embraces a veterinarily acceptable compound.

Diabetes mellitus is preferably Type 2 diabetes.

Suitably, the particularly beneficial effect on glycaemic control provided by the treatment of the invention is an improved therapeutic ratio for the combination of the invention relative to the therapeutic ratio for one compound of the combination when used alone and at a dose providing an equivalent efficacy to the combination of the invention.

In a preferred aspect the particularly beneficial effect on glycaemic control provided by the treatment of the invention is indicated to be a synergistic effect relative to the control expected from the effects of the individual active agents.

In a further aspect of the invention, combining doses of the DPP-IV inhibitor and the other agent will produce a greater beneficial effect than can be achieved for either agent alone at a dose twice that used for that agent in the combination.

Glycaemic control may be characterised using conventional methods, for example by measurement of a typically used index of glycaemic control such as fasting plasma glucose or glycosylated haemoglobin (Hb Alc). Such indices are determined using standard methodology, for example those described in: Tuescher A, Richterich, P., Schweiz. med. Wschr. 101 (1971), 345 and 390 and Frank P., 'Monitoring the Diabetic Patent with Glycosolated Hemoglobin Measurements', Clinical Products 1988.

In a preferred aspect, the dosage level of each of the active agents when used in accordance with the treatment of the invention will be less than would have been required from a purely additive effect upon glycaemic control.

It is also considered that the treatment of the invention will effect an improvement, relative to the individual agents, in the levels of advanced glycosylation end products (AGEs), and serum lipids including total cholesterol, HDL-cholesterol, LDL-cholesterol including improvements in the ratios thereof in particular an improvement in serum lipids including total cholesterol, HDL-cholesterol, LDL-cholesterol including improvements in the ratios thereof.

In the treatment of the invention, the active medicaments are preferably administered in pharmaceutical composition form. As indicated above, such compositions can include both medicaments or one only of the medicaments.

Accordingly, in one aspect the present invention also provides a pharmaceutical composition comprising a dipeptidyl peptidase IV inhibitor and another antidiabetic agent and a pharmaceutically acceptable carrier therefor.

Thus, in a further aspect, the invention also provides a process for preparing a pharmaceutical composition comprising a dipeptidyl peptidase IV inhibitor, another antidiabetic agent and a pharmaceutically acceptable carrier therefor, which process comprises admixing the dipeptidyl peptidase IV inhibitor, another antidiabetic agent and a pharmaceutically acceptable carrier.

The compositions are preferably in a unit dosage form in an amount appropriate for the relevant daily dosage.

Suitable dosages, including especially unit dosages, of the DPP-IV inhibitor or the other antidiabetic agent include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

Thus, suitable dosages for the DPP-IV inhibitors of WO 99/61431 and include those disclosed therein, for example 0.01 to 30 mg per day or 0.01 to 10 mg per kilogram of body weight. Also, the suitable doses of the other DPP-IV inhibitors mentioned herein include those mentioned in the relevant publications mentioned above.

For the alpha glucosidase inhibitor, a suitable amount of acarbose is in the range of from 25 to 600 mg, including 50 to 600 mg, for example 100 mg or 200 mg.

For the biguanide, a suitable dosage of metformin is between 100 to 3000 mg, for example 250, 500 mg, 850 mg or 1000 mg.

For the insulin secretagogue, a suitable amount of glibenclamide is in the range of from 2.5 to 20 mg, for example 10 mg or 20 mg; a suitable amount of glipizide is in the range of from 2.5 to 40 mg; a suitable amount of gliclazide is in the range of from 40 to 320 mg; a suitable amount of tolazamide is in the range of from 100 to 1000 mg; a suitable amount of tolbutamide is in the range of from 1000 to 3000 mg; a suitable amount of chlorpropamide is in the range of from 100 to 500 mg; and a suitable amount of gliquidone is in the range of from 15 to 180 mg. Also a suitable amount of glimepiride is 1 to 6 mg and a suitable amount of glipentide is 2.5 to 20 mg.

A suitable amount of repaglinide is in the range of from 0.5 mg to 20 mg, for example 16 mg. Also a suitable amount of nateglinide is 90 to 360 mg, for example 270 mg.

In one particular aspect, the composition comprises 2 to 12 mg of Compound (I).

Suitably the composition comprises 2, 3, 4, 5, 6, 7, 8, 9, 10, 11 or 12 mg of Compound (I).

Particularly, the composition comprises 2 to 4, 4 to 8 or 8 to 12 mg of Compound (I).

Particularly, the composition comprises 2 to 4 mg of Compound (I).

Particularly, the composition comprises 4 to 8 mg of Compound (I).

Particularly, the composition comprises 8 to 12 mg of Compound (I).

Preferably, the composition comprises 2 mg of Compound (I).

Preferably, the composition comprises 4 mg of Compound (I).

Preferably, the composition comprises 8 mg of Compound (I).

Suitable unit dosages of other insulin sensitisers include from 100 to 800 mg of troglitazone such as 200, 400, 600 or 800 mg or from 5 to 50 mg, including 10 to 40 mg, of pioglitazone, such as 20, 30 or 40 mg and also including 15, 30 and 45 mg of pioglitazone.

Suitable dosages of other PPARγ agonist insulin sensitisers include those disclosed for the respective agonist in the abovementioned applications, for example 2-(1-carboxy-2-{4-{2-(5-methyl-2-phenyl-oxazol-4-yl)-ethoxy]-phenyl}-ethylamino)-benzoic acid methyl ester and 2(S)-(2-benzoyl-phenylamino)-3-{4-[2-(5-methyl-2-phenyl-oxazol-4-yl)-ethoxy]-phenyl}-propionic acid are suitably dosed in accordance with the dosages disclosed in WO 97/31907.

In the treatment the medicaments may be administered from 1 to 6 times a day, but most preferably 1 or 2 times per day.

Also, the dosages of each particular active agent in any given composition can as required vary within a range of doses known to be required in respect of accepted dosage regimens for that compound. Dosages of each active agent can also be adapted as required to take into account advantageous effects of combining the agents as mentioned herein.

It will be understood that the DPP-IV inhibitor and the other antidiabetic agent are in a pharmaceutically acceptable form, including pharmaceutically acceptable derivatives such as pharmaceutically acceptable salts, esters and solvates thereof, as appropriate to the relevant pharmaceutically active agent chosen. In certain instances herein the names used for the antidiabetic agent may relate to a particular pharmaceutical form of the relevant active agent: It will be understood that all pharmaceutically acceptable forms of the active agents per se are encompassed by this invention.

The present invention also provides a pharmaceutical composition comprising a dipeptidyl peptidase IV inhibitor, another antidiabetic agent and a pharmaceutically acceptable carrier therefor, for use as an active therapeutic substance.

In particular, the present invention provides a pharmaceutical composition comprising a dipeptidyl peptidase IV inhibitor, another antidiabetic agent and a pharmaceutically acceptable carrier therefor, for use in the treatment of diabetes mellitus, especially Type 2 diabetes and conditions associated with diabetes mellitus.

Usually the compositions are adapted for oral administration. However, they may be adapted for other modes of administration, for example parenteral administration, sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dosage presentation forms for oral administration may be in tablet or capsule form and may as necessary contain conventional excipients such as binding agents, fillers, lubricants, glidants, disintegrants and wetting agents.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agent can be dissolved in the vehicle. To enhance the stability, the composition can be frozen after filling into the vial and the water removed under vacuum. Parenteral suspensions are prepared in substantially the same manner, except that the active compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions may contain from 0.1% to 99% by weight, preferably from 10-60% by weight, of the active material, depending upon the method of administration.

Examples of binding agents include acacia, alginic acid, carboxymethylcellulose calcium, carboxymethylcellulose sodium, dextrates, dextrin, dextrose, ethylcellulose, gelatin, liquid glucose, guar gum, hydroxyethyl cellulose, hydroxypropyl cellulose, hydroxypropyl methylcellulose, magnesium aluminium silicate, maltodextrin, methyl cellulose, polymethacrylates, polyvinylpyrrolidone, pregelatinised starch, sodium alginate, sorbitol, starch, syrup, tragacanth.

Examples of fillers include calcium carbonate, calcium phosphate, calcium sulphate, carboxymethylcellulose calcium, carboxymethylcellulose sodium, compressible sugar, confectioner's sugar, dextrates, dextrin, dextrose, dibasic calcium phosphate dihydrate, dibasic calcium phosphate, fructose, glyceryl palmitostearate, glycine, hydrogenated vegetable oil-type 1, kaolin, lactose, maize starch, magnesium carbonate, magnesium oxide, maltodextrin, mannitol, microcrystalline cellulose, polymethacrylates, potassium chloride, powdered cellulose, pregelatinised starch, sodium chloride, sorbitol, starch, sucrose, sugar spheres, talc, tribasic calcium phosphate, xylitol.

Examples of lubricants include calcium stearate, glyceryl monostearate, glyceryl palmitostearate, magnesium stearate, microcrystalline cellulose, sodium benzoate, sodium chloride, sodium lauryl sulphate, stearic acid, sodium stearyl fumarate, talc, zinc stearate.

Examples of glidants include colloidal silicon dioxide, powdered cellulose, magnesium trisilicate, silicon dioxide, talc.

Examples of disintegrants include alginic acid, carboxymethylcellulose calcium, carboxymethylcellulose sodium, colloidal silicon dioxide, croscarmellose sodium, crospovidone, guar gum, magnesium aluminium silicate, microcrystalline cellulose, methyl cellulose, polyvinylpyrrolidone, polacrilin potassium, pregelatinised starch, sodium alginate, sodium lauryl sulphate, sodium starch glycollate.

An example of a pharmaceutically acceptable wetting agent is sodium lauryl sulphate.

The compositions are prepared and formulated according to conventional methods, such as those disclosed in standard reference texts, for example the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) and Harry's Cosmeticology (Leonard Hill Books) or the above mentioned publications.

For example, the solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice.

Compositions may, if desired, be in the form of a pack accompanied by written or printed instructions for use.

No adverse toxicological effects are expected for the compositions or methods of the invention in the above mentioned dosage ranges.

Pharmacological Data

Age and weight matched male ZDF fa/fa rats (Genetic Models, Inc., Indianapolis, Ind.) were housed individually at 72° F. and 50% relative humidity with a 12 h light/dark cycle and fed PMI 5008 Formulab Diet (PMI Nutrition International, Saint Louis, Mo.).

Animals were dosed by oral gavage twice daily during the dark cycle for one week with vehicle (0.5% hydroxypropylmethylcellulose (HPMC) plus 0.1% Tween 80), 100 mg/kg isoleucine thiazolidide (Compound (II)), 5 mg/kg Compound (I) in vehicle, or 5 mg/kg Compound (I) plus 100 mg/kg Compound (II) in vehicle.

For glucose tolerance measurements, rats were treated with test compound for 7 days and given an intraperitoneal injection of a glucose solution in saline 30 minutes after the last dose of test compound.

Rats were anesthetized with isofluorane for cardiac blood collection 30 minutes after administration of the glucose solution. Serum chemistry measurements were obtained using an automated chemistry analyzer (ILab600, Instrument Laboratory, Lexington, Mass.).

DPP-IV activity was measured using the fluorogenic substrate Gly-Pro-AMC (50 mM) according to the manufacturers specification (Enzyme System Products, Livermore, Calif.). The substrate was mixed with 50 mM Tris, pH 7.8, in plasma (20% final v/v) and the samples were incubated for 5–20 min at 30° C. DPP-IV activity was determined by measuring fluorescence using a cytofluor spectrofluoremeter with the filters set at 360 nm excitation and 460 nm emission.

Results from each group (n=6) were averaged and compared to vehicle treated rats to determine significance and are shown in Table I.

The following data illustrates the invention but does not limit it in any way.

TABLE I

| | ZDF rats, treated BID for 7 days | | |
| --- | --- | --- | --- |
| | Plasma DPP-IV activity | % HbA1C (7 day change) | Plasma Glucose (30 min GTT) |
| Control | 5544 ± 485 | 1.63 ± 1.12 | 695 ± 24 |
| Compound (I) (5 mg/kg) | 4104 ± 399* | 0.79 ± 0.54* | 665 ± 40 |
| Compound (II) (100 mg/kg) | 962 ± 53* | 1.81 ± 1.24 | 684 ± 60 |
| Combination | 703 ± 16* | 0.41 ± 0.28* | 454 ± 52* |

*P. 0.05

The invention claimed is:

1. A method for the treatment of Type 2 diabetes mellitus and conditions associated therewith in a mammal consisting of administering:
    a dipeptidyl peptidase IV inhibitor; and
    5-[4-[2[(N-methyl-N-(2-pyridyl)amino)ethoxy]benzyl] thiazolidine-2,4-dione or a salt thereof.
2. A pharmaceutical composition consisting of:
    a dipeptidyl peptidase IV inhibitor;
    5-[4-[2[(N-methyl-N-(2-pyridyl)amino)ethoxy]benzyl] thiazolidine-2,4-dione or a salt thereof; and
    one or more pharmaceutically acceptable carrier.
3. A combination consisting of:
    a dipeptidyl peptidase IV inhibitor; and
    5-[4-[2[(N-methyl-N-(2-pyridyl)amino)ethoxy]benzyl] thiazolidine-2,4-dione or a salt thereof.

* * * * *